(12) United States Patent
Hanley et al.

(10) Patent No.: US 8,414,501 B2
(45) Date of Patent: Apr. 9, 2013

(54) THERMAL MONITORING

(75) Inventors: Brian M. Hanley, Framingham, MA (US); Michael S. H. Chu, Brookline, MA (US); Kenneth J. Daignault, Holden, MA (US); Aidan Petrie, Jamestown, RI (US); Justin Sirotin, Providence, RI (US); David Robson, Riverside, RI (US); Andrew W. Marsella, Boston, MA (US); Dan Nelsen, East Greenwich, RI (US); Michael Weiser, Groton, MA (US); Ramin N. Tehrani, West Roxbury, MA (US)

(73) Assignee: Medifocus, Inc., Columbia, MD (US)

( * ) Notice: Subject to any disclaimer, the term of this patent is extended or adjusted under 35 U.S.C. 154(b) by 412 days.

(21) Appl. No.: 12/342,959

(22) Filed: Dec. 23, 2008

(65) Prior Publication Data

US 2009/0171238 A1    Jul. 2, 2009

Related U.S. Application Data

(60) Provisional application No. 61/017,297, filed on Dec. 28, 2007.

(51) Int. Cl.
| | | |
|---|---|---|
| *A61B 5/00* | (2006.01) | |
| *G01K 1/08* | (2006.01) | |
| *G01K 1/00* | (2006.01) | |
| *A61M 29/00* | (2006.01) | |

(52) U.S. Cl.
USPC ........... 600/549; 374/158; 374/208; 374/209; 606/191; 606/192; 606/197; 606/198

(58) Field of Classification Search .................. 600/549, 600/31, 201–209, 218–235; 606/191, 192, 606/197, 198; 374/100, 158, 208, 209, 113; 604/96.01, 104
See application file for complete search history.

(56) References Cited

U.S. PATENT DOCUMENTS

| | | |
|---|---|---|
| 4,046,139 A | 9/1977 | Horn |
| 5,335,669 A | 8/1994 | Tihon et al. |
| 5,385,544 A | 1/1995 | Edwards et al. |
| 5,404,881 A | 4/1995 | Cathaud et al. |
| 5,540,655 A | 7/1996 | Edwards et al. |

(Continued)

FOREIGN PATENT DOCUMENTS

WO    WO-2007044114 A2    4/2007

*Primary Examiner* — Sean P Dougherty
*Assistant Examiner* — Devin Henson
(74) *Attorney, Agent, or Firm* — Merek, Blackmon & Voorhees, LLC

(57) ABSTRACT

A rectal thermal monitor for transrectal prostate temperature measurement includes a handle arranged in a proximal end portion of the monitor for gripping by a user, an elongate shaft extending from the handle, and an expandable distal probe portion arranged on a distal end of the shaft. The distal probe portion is arranged at a position opposite the handle portion, and is shaped to facilitate insertion through an anal sphincter and into a rectum of a patient. A cover element, is provided for covering at least a portion of the distal probe portion, and is made from a resilient material. A temperature sensing element is arranged within the distal probe portion, beneath the cover element, and is adapted and configured to sense a temperature of the prostate of the patient through the rectum wall of the patient. Further, and actuator can be provided to actuate the expandable distal probe portion, to increase a diameter thereof.

3 Claims, 12 Drawing Sheets

U.S. PATENT DOCUMENTS

| | | | |
|---|---|---|---|
| 5,666,954 A | 9/1997 | Chapelon et al. | |
| 5,674,240 A * | 10/1997 | Bonutti et al. | 606/198 |
| 5,792,070 A * | 8/1998 | Kauphusman et al. | 600/549 |
| 5,795,289 A * | 8/1998 | Wyttenbach | 600/207 |
| 5,865,788 A | 2/1999 | Edwards et al. | |
| 5,871,449 A * | 2/1999 | Brown | 600/474 |
| 6,009,351 A | 12/1999 | Flachman | |
| 6,142,993 A * | 11/2000 | Whayne et al. | 606/41 |
| 6,348,039 B1 | 2/2002 | Flachman et al. | |
| 6,348,056 B1 * | 2/2002 | Bates et al. | 606/114 |
| 6,402,742 B1 | 6/2002 | Blewett et al. | |
| 6,419,653 B2 | 7/2002 | Edwards et al. | |
| 6,475,140 B1 | 11/2002 | Konstorum et al. | |
| 6,477,426 B1 | 11/2002 | Fenn et al. | |
| 6,490,488 B1 | 12/2002 | Rudie et al. | |
| 6,592,579 B2 | 7/2003 | Arndt et al. | |
| 6,610,054 B1 | 8/2003 | Edwards et al. | |
| 6,659,963 B2 * | 12/2003 | Kaufman et al. | 600/549 |
| 6,712,771 B2 * | 3/2004 | Haddock et al. | 600/549 |
| 6,743,226 B2 | 6/2004 | Cosman et al. | |
| 6,788,977 B2 | 9/2004 | Fenn et al. | |
| 6,814,712 B1 | 11/2004 | Edwards et al. | |
| 6,824,516 B2 | 11/2004 | Batten et al. | |
| 6,852,091 B2 | 2/2005 | Edwards et al. | |
| 6,868,290 B2 | 3/2005 | Bolmsjö | |
| 6,875,209 B2 * | 4/2005 | Zvuloni et al. | 606/21 |
| 6,895,282 B2 | 5/2005 | Gellman et al. | |
| 7,819,817 B2 * | 10/2010 | Rahn | 600/549 |
| 2002/0068877 A1 * | 6/2002 | Abramovitch et al. | 600/549 |
| 2004/0176699 A1 * | 9/2004 | Walker et al. | 600/549 |
| 2005/0222517 A1 * | 10/2005 | Tiesma et al. | 600/549 |
| 2005/0281314 A1 | 12/2005 | Fraden | |
| 2007/0047618 A1 | 3/2007 | Howanski | |
| 2007/0093880 A1 * | 4/2007 | Reever | 607/100 |
| 2008/0172080 A1 * | 7/2008 | Isham | 606/192 |

* cited by examiner

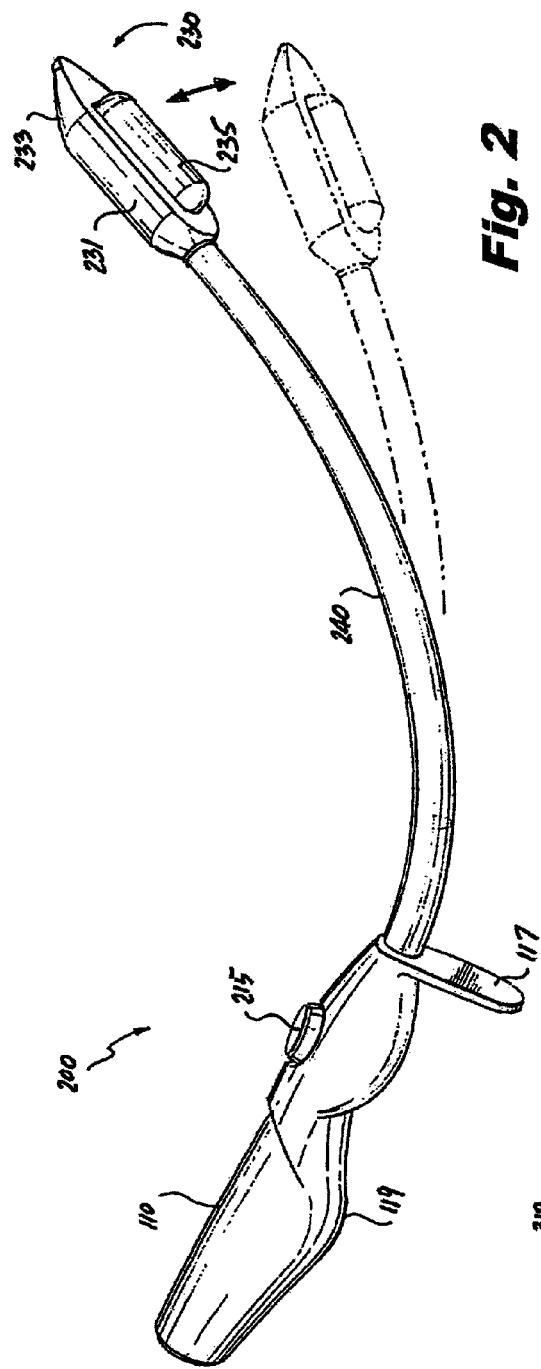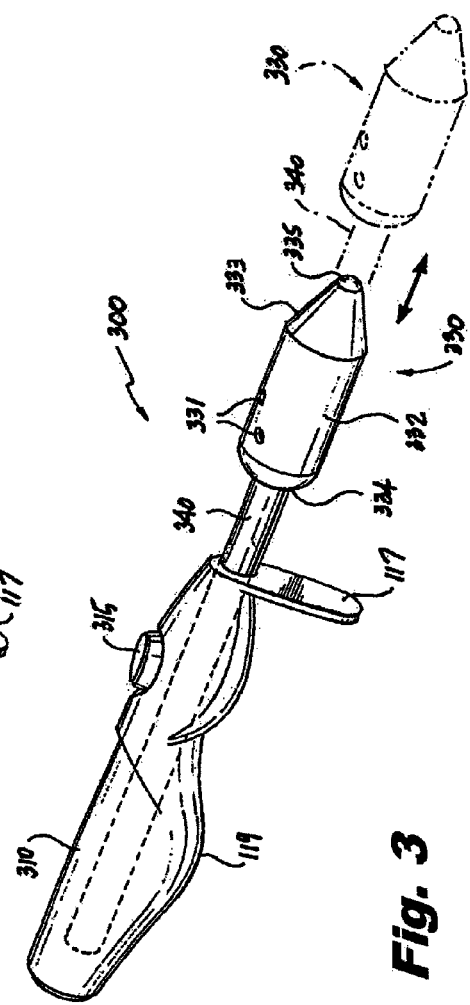
Fig. 2
Fig. 3

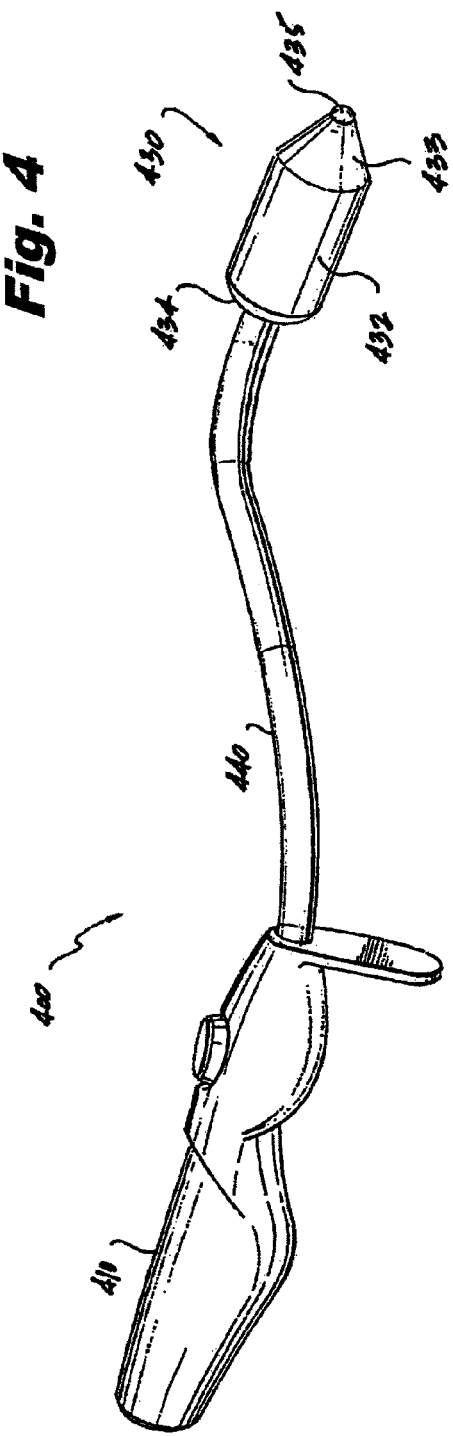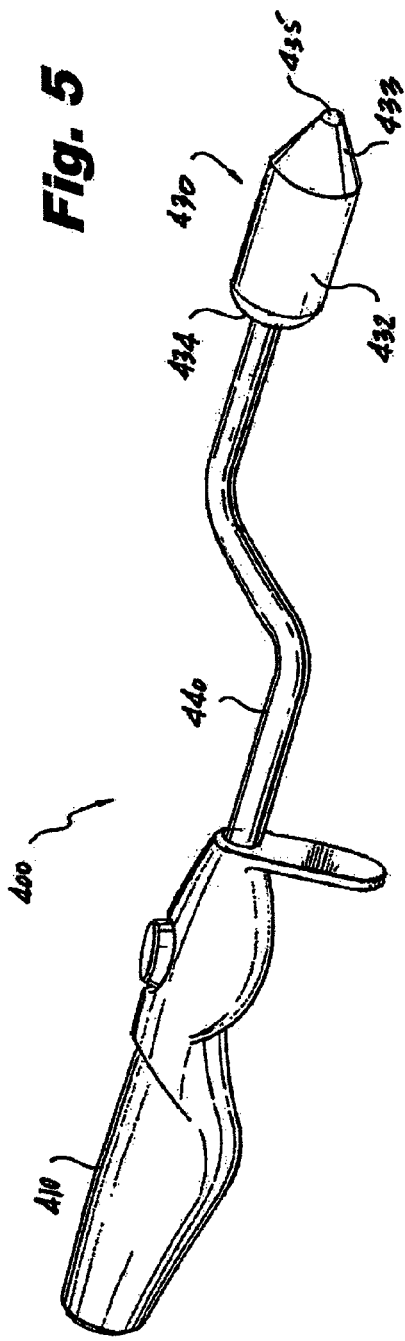

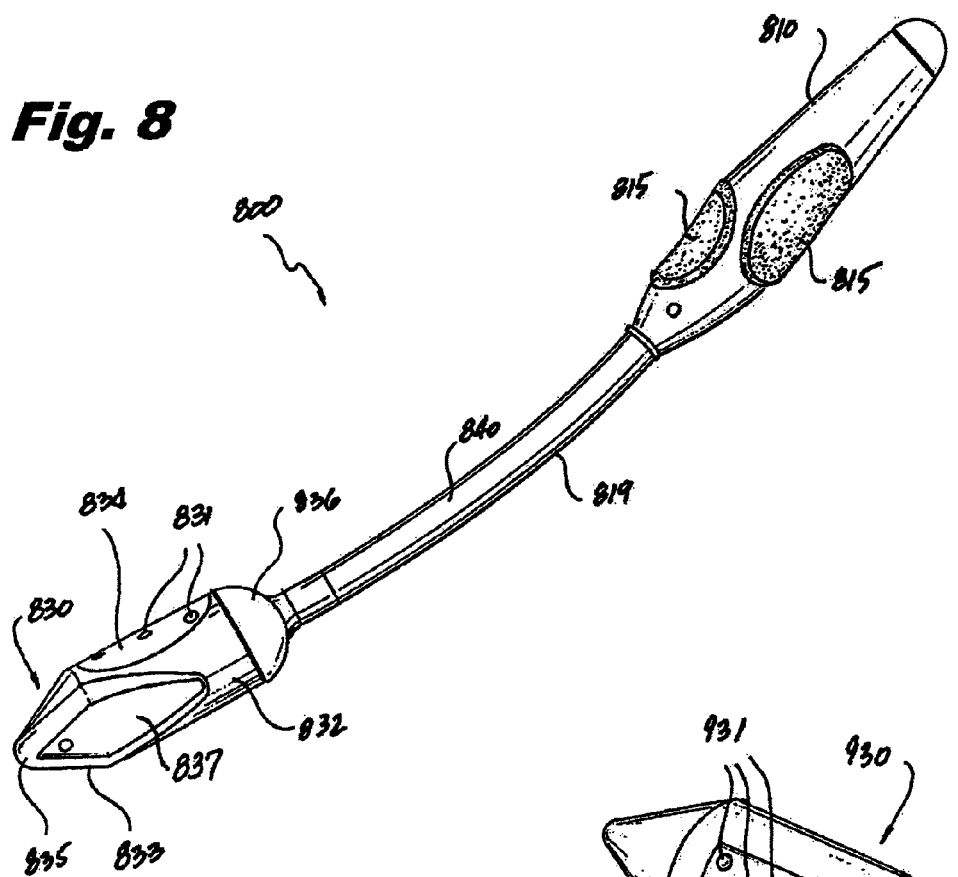
Fig. 8
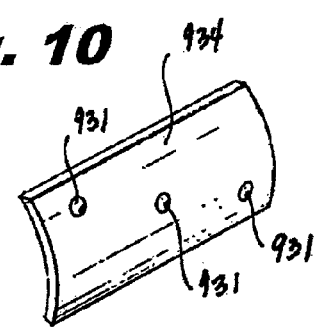
Fig. 10
Fig. 9

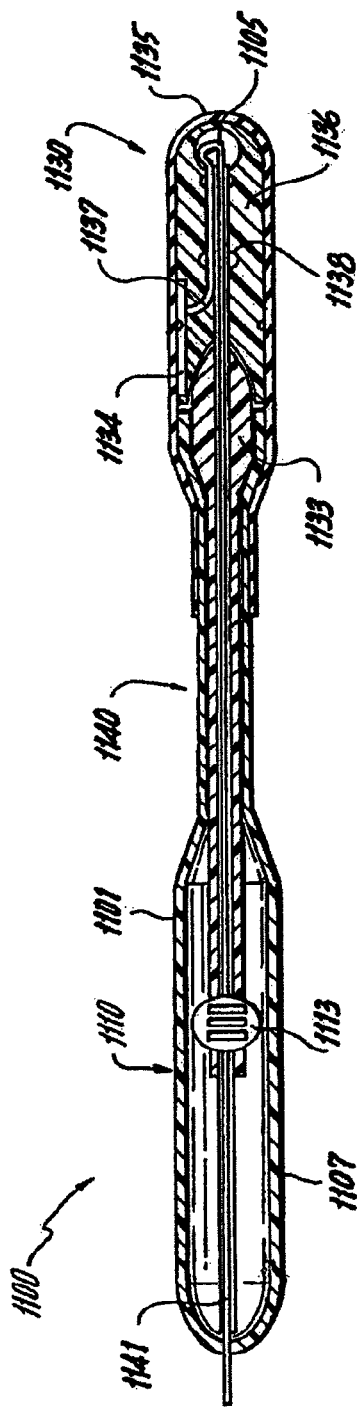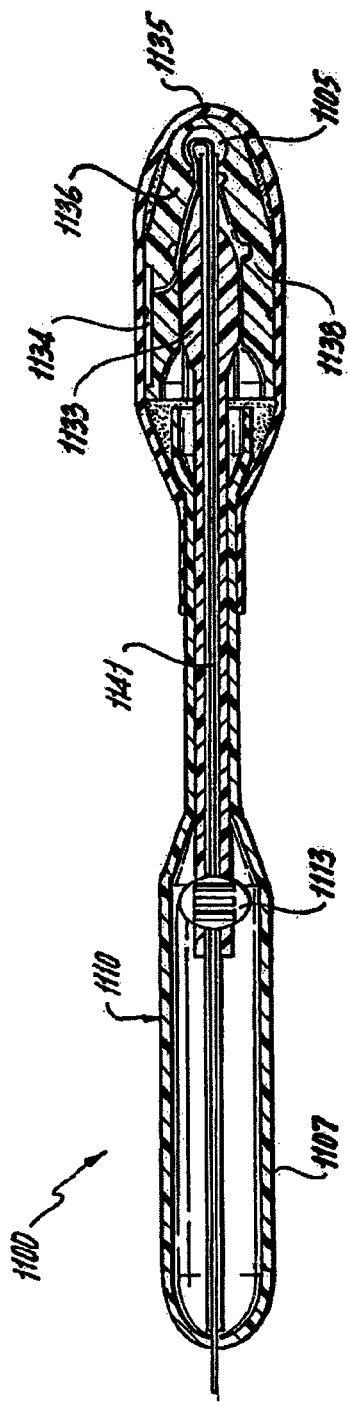

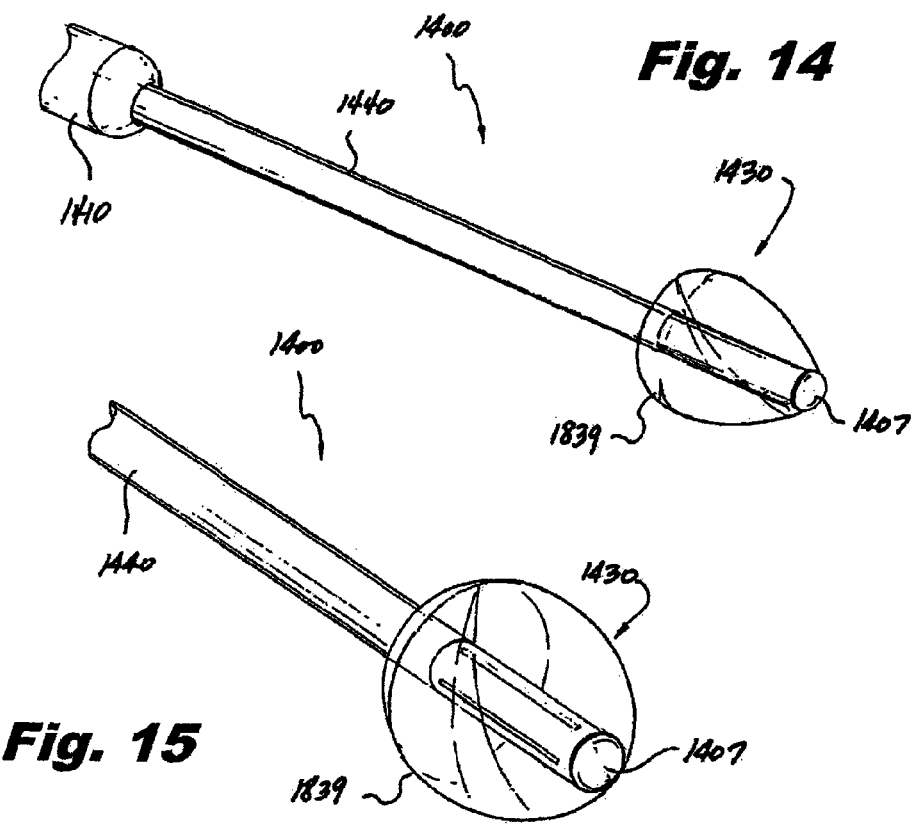
Fig. 14
Fig. 15
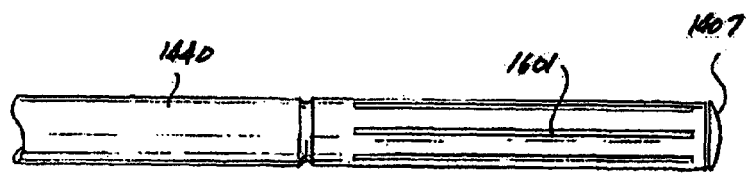
Fig. 16
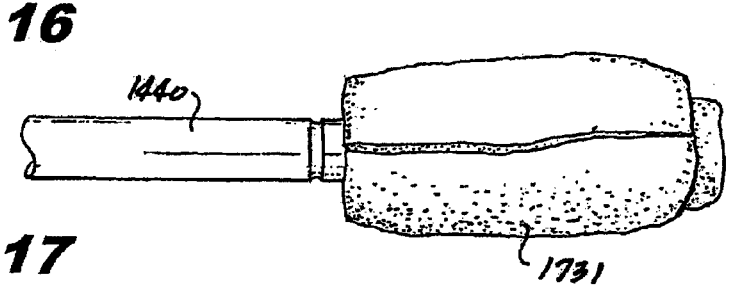
Fig. 17

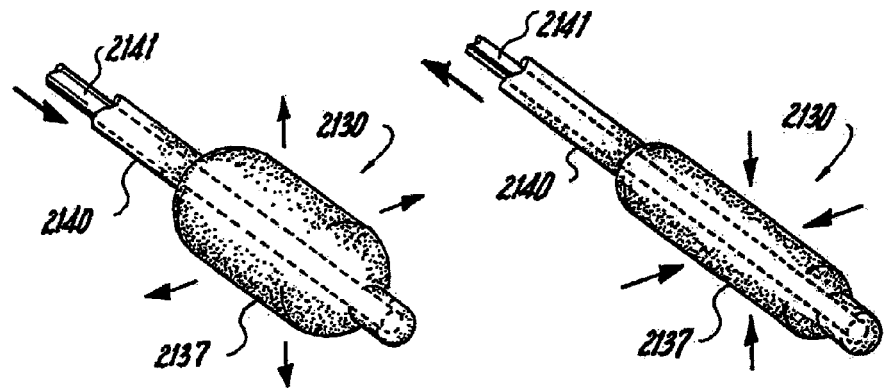
Fig. 22a  Fig. 22b
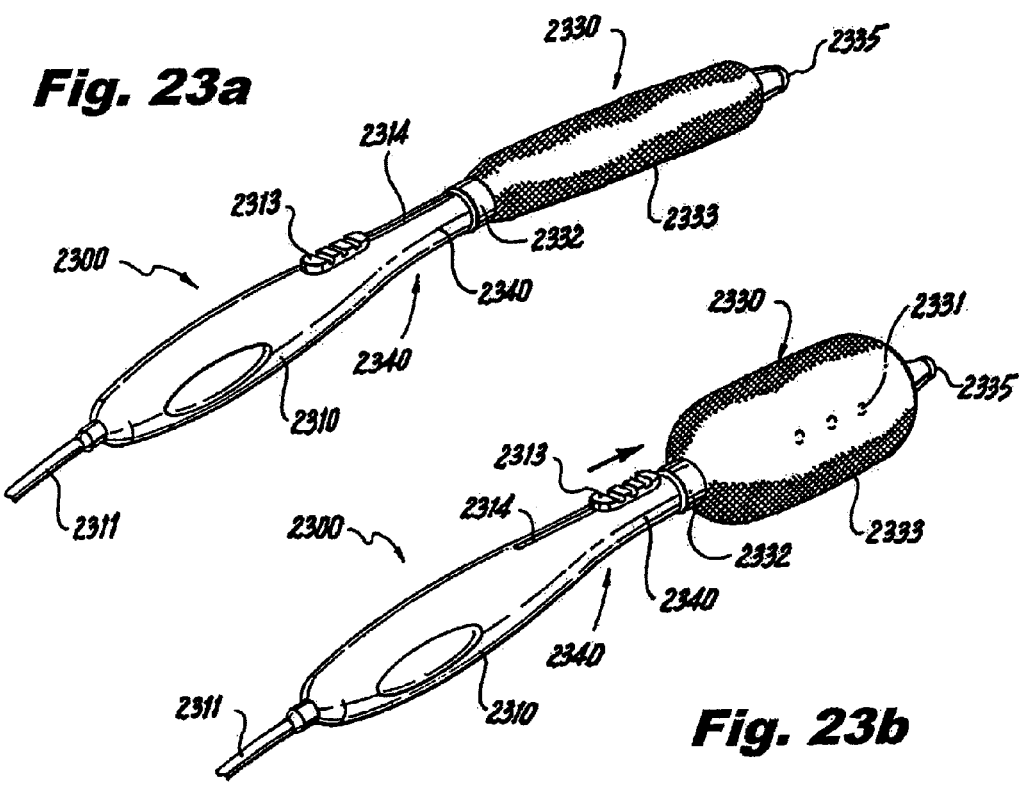
Fig. 23a  Fig. 23b

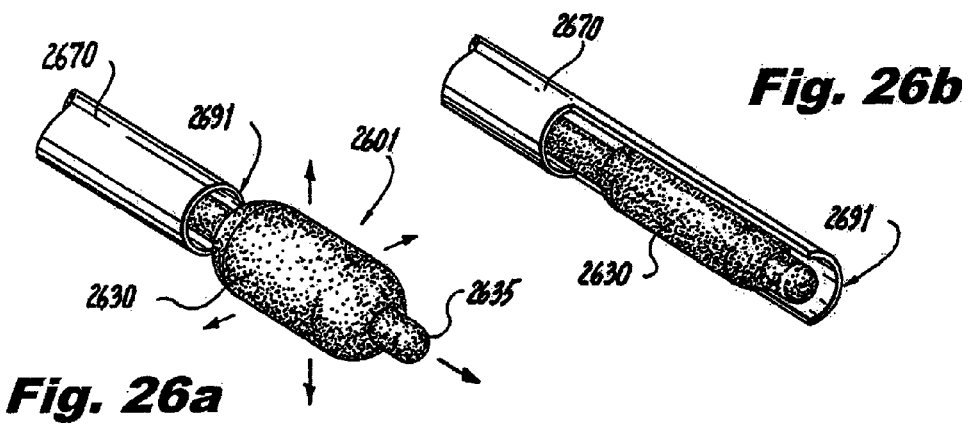
Fig. 26a
Fig. 26b
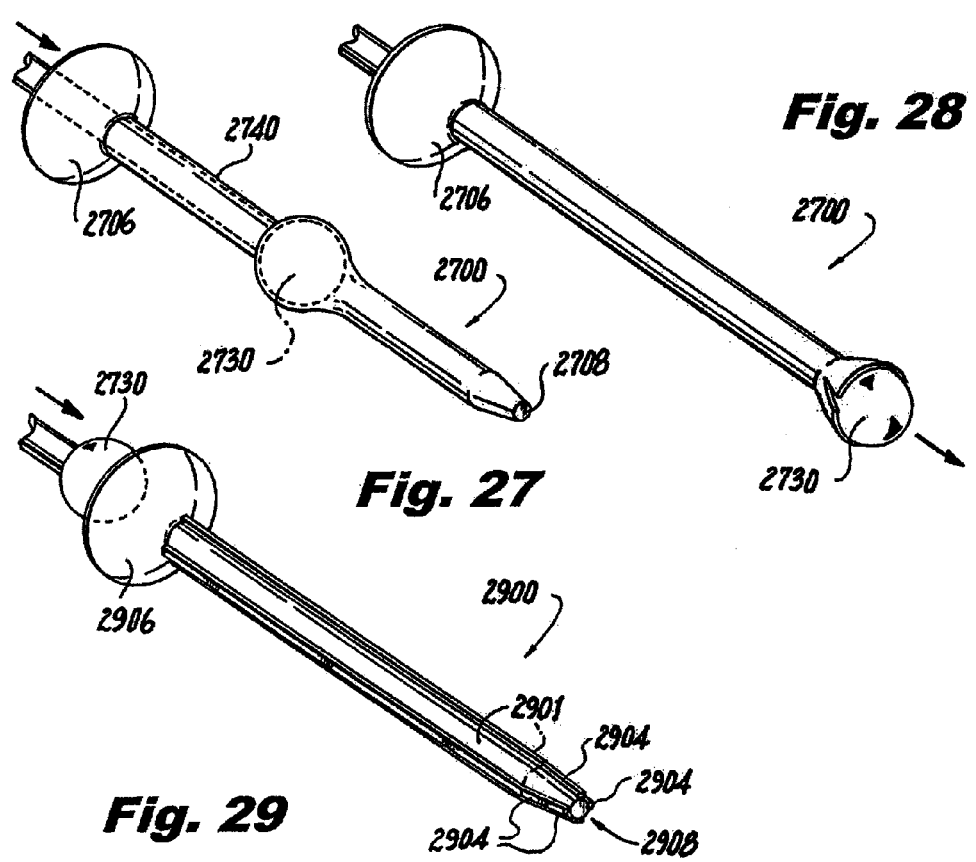
Fig. 27
Fig. 28
Fig. 29

THERMAL MONITORING

CROSS-REFERENCE TO RELATED CASES

This application claims priority to, and the benefit of Provisional U.S. Patent Application Ser. No. 61/017,297, filed Dec. 28, 2007, the entirety of which is incorporated herein by reference.

TECHNICAL FIELD

This disclosure generally relates to monitoring a biological parameter after insertion of a medical device or a portion of the medical device into a body cavity and, more particularly, to a probes that allow for comfortable and easy insertion into the body cavity. A rectal thermal monitor (RTM) can be used to monitor temperature of the prostate gland, for example, during microwave or some other therapy or therapies for treatment of benign prostatic hyperplasia (BPH).

BACKGROUND INFORMATION

The prostate gland is part of the male reproductive system, and consists of two lobes in front of the rectum, just below the bladder. The prostate gland surrounds the urethra, the channel through which urine passes out of the body. The prostate gland has two main periods of growth, the first of which occurs during puberty. However, during a man's mid-twenties, the prostate gland begins to grow again and continues to do so for the remainder of life. As the prostate gland grows, several problems often occur as a result of excessive growth. Rarely do such afflictions occur before the age of forty, but as a man's age increases, the likelihood of prostate gland afflictions increases significantly.

Benign prostatic hyperplasia (BPH) is the later growth of the prostate gland, which can cause symptoms such as pain, frequent urination and inability to fully empty one's bladder. Fortunately, a digital rectal exam can often lead to early detection of BPH, for which several effective treatment modalities exist. For example, drugs such as finasteride, transurethral microwave procedures, transurethral needle ablation, and surgical treatments are available.

Several approaches to treatment by heating the prostate are known. These approaches generally have difficulty in targeting the prostate without destroying healthy tissue. As a result, monitoring of the temperature of the prostate and surrounding areas is critical to safe and successful procedures. In order to measure accurately the rectal wall temperature and, thereby, monitor the prostate temperature, it is necessary that a probe of sufficient size be provided to press against the rectal wall at the appropriate location. However, probes of such size can cause pain and discomfort, at least upon insertion. Known techniques for monitoring internal temperature can provide not only poor performance but also discomfort during insertion.

SUMMARY OF THE INVENTION

The invention generally relates to rectal thermal monitors (RTMs), and more particularly to RTMs that improve upon the aforementioned problems with existing temperature monitors. The purposes and advantages of the invention will be set forth in and apparent from the description, drawings, and claims that follow.

The invention generally relates to a probe that is easily inserted into the body of a patient (human or other animal) that is comfortable for the patient during insertion, during a procedure, and during removal from the patient, while still effectively engaging an internal wall of the patient's body (such as the internal wall of the patient's rectum) after insertion into the patient's body.

In accordance with one aspect of the invention, a rectal thermal monitor for transrectal prostate temperature measurement is provided. The monitor includes a handle, an elongate shaft, an expandable probe portion, a cover element and at least one temperature sensing element. The handle is arranged in a proximal end portion of the monitor for gripping by a user, and the elongate shaft extends from the handle. The expandable distal probe portion is arranged on a distal end of the shaft, at a position opposite the handle portion, and is shaped to facilitate insertion through the anal sphincter and into the rectum of a patient. The distal probe portion includes flexible arms, capable of being compressed to a low-profile configuration prior to insertion into the rectum of a the patient. The cover element covers at least a portion of the distal probe portion and is made from a resilient material. The temperature sensing element is arranged within the distal probe portion, beneath the cover element, and is adapted and configured to sense a temperature of the prostate through the rectum wall of the patient.

Embodiments of this aspect other aspects of the invention can include one or more of the following features. The monitor can further include a stop, secured to the monitor at a predetermined position, for preventing insertion of the monitor into a rectum of a patient beyond a predetermined point. The temperature sensing element can be attached to a heat sink to facilitate temperature measurement of an increased area. Further, the heat sink can be insert molded into the distal probe portion.

In accordance with another aspect of the invention, a rectal thermal monitor for transrectal prostate temperature measurement is provided. The monitor includes a handle, an elongate shaft, an expandable probe portion, a cover element and at least one temperature sensing element. The handle is arranged in a proximal end portion of the monitor for gripping by a user, and the elongate shaft extends from the handle. The expandable distal probe portion is arranged on a distal end of the shaft, at a position opposite the handle portion, and is shaped to facilitate insertion through the anal sphincter and into the rectum of a patient. The expandable distal probe portion includes two probe halves, each arranged on a separate half shaft. The cover element covers at least a portion of the distal probe portion and is made from a resilient material. The temperature sensing element is arranged within the distal probe portion, beneath the cover element, and is adapted and configured to sense a temperature of the prostate through the rectum wall of the patient.

Embodiments of this aspect other aspects of the invention can include one or more of the following features. The distal probe portion can include a tapered distal end to facilitate insertion through the anal sphincter. The temperature sensing element can be attached to a heat sink to facilitate temperature measurement of an increased area. The monitor can further comprise an inflatable bladder arranged between the two probe halves, inflation of which increases the diameter of the distal probe portion. Further, one of the half shafts and probe halves can be slideable with respect to the other.

In accordance with still another aspect of the invention, a rectal thermal monitor for transrectal prostate temperature measurement is provided. The monitor includes a handle, an elongate shaft, an expandable probe portion, a cover element and at least one temperature sensing element. The handle is arranged in a proximal end portion of the monitor for gripping by a user, and the elongate shaft extends from the handle. The expandable distal probe portion is arranged on a distal end of the shaft, at a position opposite the handle portion, and is shaped to facilitate insertion through the anal sphincter and into the rectum of a patient. The expandable distal probe portion includes an inflatable bladder on one side thereof, inflation of which increases the size of the distal probe portion. The cover element covers at least a portion of the distal probe portion and is made from a resilient material. The temperature sensing element is arranged within the distal probe portion, beneath the cover element, and is adapted and configured to sense a temperature of the prostate through the rectum wall of the patient.

Embodiments of this aspect other aspects of the invention can include one or more of the following features. The temperature sensing element can be attached to a heat sink to facilitate temperature measurement of an increased area, and the heat sink can be insert molded into the distal probe portion. The monitor can further include a valve to allow pressurized fluid to enter the bladder and/or a pump to provide pressurized fluid to the bladder.

In accordance with a further aspect of the invention, a rectal thermal monitor for transrectal prostate temperature measurement is provided. The monitor includes a handle, an elongate shaft, an expandable probe portion, an actuator, a cover element and at least one temperature sensing element. The handle is arranged in a proximal end portion of the monitor for gripping by a user, and the elongate shaft extends from the handle. The expandable distal probe portion is arranged on a distal end of the shaft, at a position opposite the handle portion, and is shaped to facilitate insertion through the anal sphincter and into the rectum of a patient. The probe portion includes one or more inner cam following surfaces, while the actuator includes one or more movable cams, actuated by a user, which urge the cam following surfaces radially outwardly. The cover element covers at least a portion of the distal probe portion and is made from a resilient material. The temperature sensing element is arranged within the distal probe portion, beneath the cover element, and is adapted and configured to sense a temperature of the prostate through the rectum wall of the patient.

Embodiments of this aspect other aspects of the invention can include the following feature. The cover element can cover substantially the entire distal probe portion.

In accordance with an additional aspect of the invention, a rectal thermal monitor for transrectal prostate temperature measurement is provided. The monitor includes a handle, an elongate shaft, an expandable probe portion, a cover element and at least one temperature sensing element. The handle is arranged in a proximal end portion of the monitor for gripping by a user, and the elongate shaft extends from the handle. The expandable distal probe portion is arranged on a distal end of the shaft, at a position opposite the handle portion, and is shaped to facilitate insertion through the anal sphincter and into the rectum of a patient. The expandable distal probe portion includes an expandable mesh, one end of which is secured to a distal end of the shaft, and the other end of which is secured to a movable element, distal movement of which causes radial outward expansion of the probe portion. The cover element covers at least a portion of the distal probe portion and is made from a resilient material. The temperature sensing element is arranged within the distal probe portion, beneath the cover element, and is adapted and configured to sense a temperature of the prostate through the rectum wall of the patient.

In accordance with a further aspect of the invention, a rectal thermal monitor for transrectal prostate temperature measurement is provided. The monitor includes a handle, an elongate shaft, an expandable probe portion, a cover element and at least one temperature sensing element. The handle is arranged in a proximal end portion of the monitor for gripping by a user, and the elongate shaft extends from the handle. The expandable distal probe portion is arranged on a distal end of the shaft, at a position opposite the handle portion, and is shaped to facilitate insertion through the anal sphincter and into the rectum of a patient. The distal probe portion includes a resilient spiral member, relative rotation of the inner and outer coaxial members causing expansion or contraction of the probe portion. The cover element covers at least a portion of the distal probe portion and is made from a resilient material. The temperature sensing element is arranged within the distal probe portion, beneath the cover element, and is adapted and configured to sense a temperature of the prostate through the rectum wall of the patient.

Embodiments of this aspect other aspects of the invention can include the following feature. The shaft can extend past the distal probe portion to a distal end of the monitor.

In accordance with still another aspect of the invention, a rectal thermal monitor for transrectal prostate temperature measurement is provided. The monitor includes a handle, a user-shapeable elongate shaft, an expandable probe portion, a cover element and at least one temperature sensing element. The handle is arranged in a proximal end portion of the monitor for gripping by a user, and the user-shapeable shaft extends from the handle and facilitates navigation of the anatomy of a patient. The expandable distal probe portion is arranged on a distal end of the shaft, at a position opposite the handle portion, and is shaped to facilitate insertion through the anal sphincter and into the rectum of a patient. The cover element covers at least a portion of the distal probe portion and is made from a resilient material. The temperature sensing element is arranged within the distal probe portion, beneath the cover element, and is adapted and configured to sense a temperature of the prostate through the rectum wall of the patient.

Embodiments of this aspect other aspects of the invention can include the following feature. The shaft can extend past the distal probe portion to a distal end of the monitor.

In accordance with another aspect of the invention, a method is provided, which includes the steps of providing a rectal thermal monitor according to any one or more of the foregoing embodiments, for example, and inserting a distal probe portion of that monitor into the rectum of the patient. The distal probe portion is then expanded within the rectum of the patient. The method further includes orienting the distal probe portion within the rectum of the patient to obtain an accurate temperature reading of a prostate gland of the patient, and measuring a temperature of the prostate gland. The method also includes collapsing the distal probe portion, upon completion of a procedure and removing the distal probe portion from the rectum.

Both the foregoing description and the following description are exemplary and not limiting.

BRIEF DESCRIPTION OF THE DRAWINGS

The accompanying drawings, which are incorporated in and constitute part of this specification, are included to illustrate and provide a further understanding of the invention. Together with the description, the drawings serve to explain the principles of the invention, wherein:

FIG. 2 is a side view of a second representative embodiment of a rectal thermal monitor in accordance with the present invention, which includes an inflatable bladder on one side of the probe end.

FIG. 3 is an isometric view of a third representative embodiment of a rectal thermal monitor in accordance with the present invention, which includes an extendible shaft.

FIGS. 4 and 5 are side views of a fourth representative embodiment of a rectal thermal monitor in accordance with the present invention, illustrating different positions of a probe end, which is connected to a handle by way of a flexible shaft.

FIGS. 6 and 7 are isometric views of a fifth representative embodiment of a rectal thermal monitor in accordance with the present invention, wherein FIG. 6 illustrates flexible arms in an expanded state, and FIG. 7 illustrates the arms in a compressed state.

FIG. 8 is an isometric view of a sixth representative embodiment of a rectal thermal monitor in accordance with the present invention, which includes a tapered probe end and a curved shaft to facilitate probe placement.

FIG. 9 is an isometric view of a probe end including a heat sink provided therein, in accordance with the invention.

FIG. 10 is an isometric view of a heat sink for use with one or more temperature sensors in accordance with the invention.

FIGS. 11a and 11b are cross-sectional views of a seventh representative embodiment of a rectal thermal monitor in accordance with the present invention, which includes a mechanical cam feature that enables radial outward expansion of the probe end. FIG. 11a illustrates the probe end in its contracted state, and FIG. 11b illustrates the probe end in its expanded state.

FIG. 12a illustrates the probe end in its contracted state, and FIG. 12b illustrates the probe end in its expanded state.

FIG. 12b illustrates the probe end in its contracted state, and FIG. 12a illustrates the probe end in its expanded state.

FIGS. 14 and 15 are isometric views of an eighth representative embodiment of a rectal thermal monitor in accordance with the present invention, which includes a compliant probe end, covered in a flexible sheath.

FIG. 16 illustrates a shaft from the embodiment of FIGS. 14 and 15 with the probe end removed.

FIG. 17 illustrates a shaft from the embodiment of FIGS. 14 and 15 with the flexible sheath removed, illustrating only a compliant material filling attached to the shaft.

FIGS. 22a and 22b are schematic illustrations of a rectal thermal monitor of FIG. 21, illustrating the rectal thermal monitor in a relaxed state (FIG. 22a) and in a stretched state (FIG. 22b).

FIGS. 23a and 23b are side views of an eleventh representative embodiment of a rectal thermal monitor in accordance with the present invention, which includes an expandable probe end made of an expandable mesh material, which when compressed axially, expands radially.

FIGS. 26a and 26b are schematic diagrams illustrating an exemplary rectal thermal monitor in accordance with the invention having a collapsible probe end. FIG. 26b illustrates the probe end compressed within the sleeve, prepared for insertion through the anal sphincter of a patient, while FIG. 26a illustrates the expanded probe end outside of the sleeve.

FIG. 27 illustrates an insertion sleeve, which can be inserted prior to insertion of rectal thermal monitors in accordance with the invention, which allows for easier insertion of the rectal thermal monitor.

FIG. 28 illustrates the sleeve of FIG. 27, illustrating the rupturable capability of the distal end thereof, when the probe end is pushed through the sleeve and into the rectum of the patient.

FIG. 29 illustrates a sleeve in accordance with the invention similar to that of FIG. 29, but additionally including longitudinally stiffening ribs to prevent excess elongation of the sleeve.

DESCRIPTION

The devices and methods presented herein may be used in conjunction with any probe for which easy entry into and secure retention within a body cavity, such as the rectum is desired or required. The present invention is particularly suited for temperature measurement of the rectum wall of a patient during transurethral microwave dilatation (TUMD) for treatment of BPH.

Figure 1:
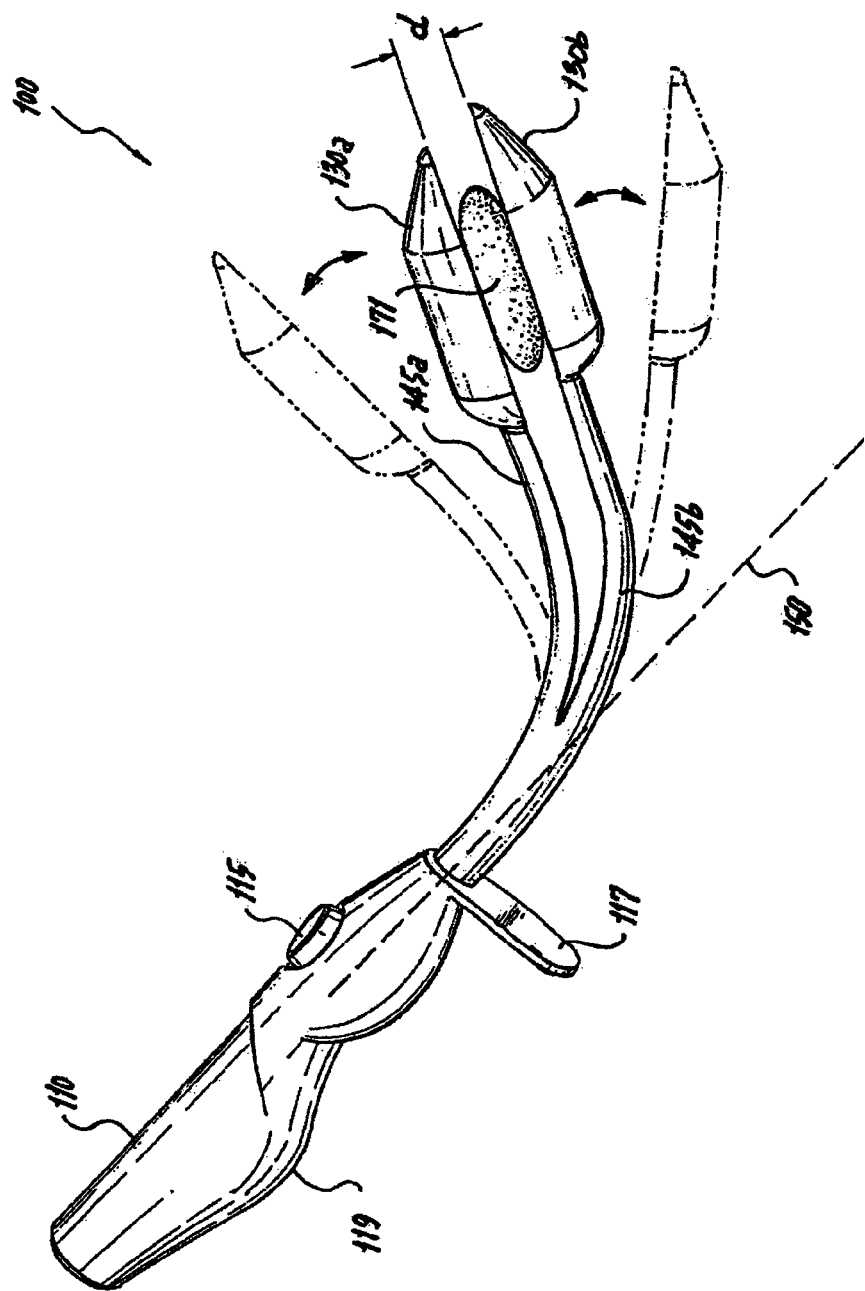
FIG. 1 is a side view of a first representative embodiment of a rectal thermal monitor (RTM) in accordance with the present invention, which includes separable probe end halves attached respectively to one of two half shafts, to impart expandability to the probe end.

FIG. 1 illustrates a first embodiment of a rectal thermal monitor (RTM) in accordance with the invention, designated generally by reference number 100. The rectal thermal monitor 100 includes a handle portion 100, arranged at a proximal end portion, and an expandable probe end 130a, 130b arranged at a distal end portion. As illustrated, the handle is provided with a contour 119, to facilitate a secure and comfortable grip by a user, such as by a physician or technician. A detent on one or more sides can be provided in order to facilitate engagement with the user's thumb, to help minimize slippage in the user's hand.

A stop 117 is provided in a predetermined location along the length of the rectal thermal monitor 100. The stop 117 acts as a guide to the user to prevent the rectal thermal monitor from being inserted excessively into the rectum. The stop 117 can be fixed relative to the body of the rectal thermal monitor 100, or can be adjustably secured thereto with, for example, a friction fit, snap fit, locking clip, thumbscrew, or other adjustable locking component.

Two half shafts 145a, 145b extend from the handle portion 110. In the embodiment of FIG. 1, the upper half shaft 145a is slideable with respect to the lower half shaft 145b and the handle portion 110. Alternatively, the lower half shaft 145b can be slideable with respect to the upper half shaft 145a and the handle portion 110. In either case, sliding would occur along line 150, which is shown as a dashed line. Alternatively still, one or both of the half shafts 145a, 145b can pivot or flex with respect to the handle portion 110 to effect expansion of the probe ends 130a, 130b.

In other variations, an inflatable bladder can be provided between the probe ends 130a, 130b that when inflated, effects relative displacement of the probe ends 130a, 130b. One or more temperature sensors are configured in one or both of the probe ends 130a, 130b, in one embodiment toward the other circumference thereof. Conductive wires are provided from the temperature sensor(s) through one or both half shafts 145a, 145b, through the handle portion 110. A connector can be supplied on the handle portion 110 to connect external equipment, such as a Transurethral Microwave Thermotherapy (TUMT) console.

The desired result is the relative displacement of probe ends 130a, 130b from one another by a distance "d", so that one of the probe ends 130a, 130b can securely contact the rectum wall in the region of a patient's prostate gland. Due to the geometry of the male anatomy, to enable comfortable insertion, the lower probe end 130b, which is on the convex side of the curve of the rectal thermal monitor 100, is provided with a temperature sensor, which will be described in more detail below. Such a temperature sensor can include three thermocouples in contact with a heat sink.

The shape of probe ends 130a, 130b can be such that a tapered end is provided, as can be seen in FIG. 1. This facilitates insertion through the patient's anus and into the rectum. Once inserted, the convex, relatively bulbous shape of the probe ends 130a, 130b roughly mirrors the general shape of the inner wall of the rectum, so that once the probe ends 130a, 130 are in contact with the mucosa of the rectum wall, they are able to contact a large area thereof, to obtain an accurate temperature reading of the prostate gland through the rectum wall.

The rectal thermal monitor 100 can be composed primarily from polymeric materials, although components can include metals such as steel, copper, aluminum, alloys, shape-memory alloys, and/or composite materials as desired or required. The handle can include a material or covering of material that enhances gripping by the user, and the probe ends 130a, 130b can include a material, or covering of material that provides relatively low coefficient of friction against a patient's anatomy, to facilitate easy insertion. A relatively rigid overall structure can be provided, so that the probe ends 130a, 130b can be effectively inserted and accurately oriented with respect to the patient's anatomy. However, the probe ends 130a, 130b themselves can include a layer of compliant material, such as silicone gel, beneath the outer covering. The probe ends 130a, 130b alternatively can be made essentially in their entirety from a compliant material such as silicone rubber. In such an instance, a more rigid portion can be incorporated within the probe ends 130a, 130b to provide rigidity to each of the probe ends 130a, 130b. Polymers such as Nylon, polyethylene terephthalate (PET), or acrylonitrile butadiene styrene (ABS) can be used for relatively rigid components of the rectal thermal monitor 100. The covering, if provided, can be overmolded over the core of the rectal thermal monitor 100, and can include materials such as thermoplastic elastomers (TPE).

If manufactured from multiple pieces, such pieces can be joined in any suitable fashion, including but not limited to insert molding, overmolding, snap fit, heat, RF, ultrasonic or solvent welding or adhesives.

The rectal thermal monitor 100 can be sized such that it is both large enough to perform the necessary tasks, and small and light enough to prevent user fatigue and patient discomfort. The half shafts 145a, 145b can be long enough so that the probe ends 130a, 130b can be situated within the patient's rectum, while the handle portion 110 remains external to the patient with the stop 117 acting as a guide, and to prevent excessive insertion into the patient's rectum. Depending on the precise implementation of the invention, the probe ends 130a, 130b, when in a position for measurement of temperature, are in combination about 2.5 inches (6.25 cm) in length and about 0.5 inches (1.25 cm) in diameter. The rectal thermal monitor 100, as a whole, can be about 12 inches (30 cm) in length. Naturally, depending on the specific needs or desires, these dimensions can be altered. The stop 117 can be about one inch (2.5 cm) in length, or another length that is effective to prevent excessive insertion of the rectal thermal monitor 100, without unnecessarily interfering with necessary manipulation of the rectal thermal monitor 100.

If desired, the rectal thermal monitor 100 can be manufactured in a range of sizes for different sizes of patient. For a larger patient, it may be necessary to provide longer half shafts 145a, 145b, and/or to increase the size of the probe ends 130a, 130b.

In accordance with the invention, the handle portion 110 can be sized such that it is noticeably larger than the probe ends 130a, 130b, in order to give the illusion of smaller probe ends 130a, 130b. Accordingly, patient anxiety can be reduced, in comparison with use of a probe that the patient conceives is large. Additionally or alternatively, colors for the probe ends 130a, 130b can be selected to minimize the apparent size of the probe ends 130a, 130b. For example, the probe end can be fabricated from a dark-colored material, such as black, dark blue, or dark green. Similarly, a pattern of different colors can be utilized. For example, the probe can be provided with alternating regions of dark and light colors, in order to visually break up the probe ends 130a, 130b. A similar approach can be taken in coloring or patterning the entire rectal thermal monitor 100, including the half shafts 145a, 145b and the handle portion 110.

In use, the probe halves 130a, 130b are initially configured to be essentially adjacent to one another, resulting the lowest possible overall profile, in order to facilitate insertion. The physician or technician then inserts the probe ends 130a, 130b of the rectal thermal monitor into the anus of the patient and orients the rectal thermal monitor 100 such that the temperature sensor is in a position with respect to the rectum wall such that the temperature of the prostate gland can be monitored. An inserter or sleeve, as will be described below in connection with FIGS. 25-29 can also be used to facilitate insertion of the rectal thermal monitor 100.

The probe halves 130a, 130b are then separated by any suitable means. As set forth above, the half shafts 145a, 145b can slide or pivot with respect to one another, to separate the probe ends 130a, 130b. The actuator button 115, in the case of an embodiment where one of the half shafts 145a, 145b slides, can be configured so as to ratchet one of the half shafts 145a, 145b distally. Alternatively, if one of the half shafts 145a, 145b pivots with respect to the handle portion 110, the actuator can be rigidly connected to that shaft as a lever, for example, to pivot the probe ends 130a, 130b away from one another. If embodied with an inflatable bladder 171 (shown in phantom line) between the probe ends 130a, 130b, the actuator 115 can actuate a manual pump, to pump, or a valve to allow passage of pressurized fluid to enter the bladder 171, thereby separating the probe ends 130a, 130b. Thus, the probe ends 130a, 130b can be made to effectively abut the rectum wall.

Upon completion of the procedure, the rectal thermal monitor 100 can be configured so that the probe ends 130a, 130b passively, or actively are urged toward each other. For example, if the rectal thermal monitor 100 is provided with a valve, actuated by depressing the actuator 115, then by depressing the valve after disconnecting or turning off a pressurized fluid source will allow fluid from within the bladder 171 to be released as the rectal thermal monitor 100 is withdrawn from the rectum. The anatomy can help urge the probe ends 130a, 130b toward one another during removal.

FIG. 2 illustrates another embodiment of a rectal thermal monitor in accordance with the invention, which is designated generally by reference number 200. As can be seen, the rectal thermal monitor 200 includes a handle 110, essentially the same in appearance as the handle of the rectal thermal monitor 100 of FIG. 1. A contour 119 is provided to facilitate secure gripping, and a stop 117 is provided to prevent excessive insertion of the rectal thermal monitor 200. A curved, elongate shaft 240, in this case, is a single shaft, since the probe end 230 is a unitary structure, rather than separable halves of the rectal thermal monitor 100 of FIG. 1. The curvature of the shaft 240, as with the foregoing rectal thermal monitor 100 of FIG. 1, facilitates navigation of the anatomy of the patient.

To facilitate insertion of the rectal thermal monitor 200 into the patient's rectum, the end portion includes a taper 233 at its distalmost end. The body 231 of the end portion 231 can include a semi-rigid or rigid core, and can have a relatively compliant material arranged on its outer surface, opposite an inflatable bladder 235. One or more temperature sensors, as described in more detail below, can be provided in the body 231, so that good contact is made between the rectum wall and the probe end 230.

When inserted in the rectum, the bladder 235 is filled with fluid to urge the body 231 of the probe end 230, and thus also the temperature sensor(s) against the rectum wall. The bladder 235 is collapsible to allow for insertion into, and withdrawal from, the rectum. In this embodiment, the bladder 235 is in fluid communication with a control element, such as a valve or manual pump, actuated through the actuator or button 215. If provided with a pump, the user can depress the actuator 215 repeatedly to inflate the bladder 235. Depending on the configuration, a stopcock can be provided to relieve pressure built up within the bladder, so that the rectal thermal monitor 200 can be easily removed from the rectum of the patient.

Materials for the rectal thermal monitor 200 of FIG. 2 can include any of the foregoing materials, such as polymeric materials, metals and/or composite materials. The inflatable bladder 235 can be made of a resilient material, such as a silicone rubber, to provide adequate resiliency and durability during insertion, inflation, and withdrawal. Multiple pieces can be joined in any suitable fashion, including but not limited to insert molding, overmolding, snap fit, heat, RF, ultrasonic or solvent welding, or adhesives.

The rectal thermal monitor 200 is, as with the embodiment of FIG. 1, can be sized such that it is both large enough to perform the necessary tasks, and small and light enough to prevent user fatigue and patient discomfort. The shaft 240 can be long enough so that the probe end 230 can be situated within the patient's rectum, while the handle portion 110 remains external to the patient, with the stop 117, acting as a guide, and to prevent excessive insertion into the patient's rectum.

In one embodiment of the invention, the probe end 230, with the bladder 235 fully inflated and in a position for measurement of temperature, is about 2.5 inches (6.25 cm) in length and about 0.5 inches (1.25 cm) in diameter. The rectal thermal monitor 200 can be about 12 inches (30 cm) in length overall. Depending on the needs or desires, these dimensions can be changed accordingly. The stop 117 can be sized to be about one inch (2.5 cm) in length. Other sizes or shapes that are effective to prevent excessive insertion of the rectal thermal monitor 200, without unnecessarily interfering with necessary manipulation of the rectal thermal monitor 200 can alternatively be used. As with the foregoing embodiment of FIG. 1, the rectal thermal monitor 200 can be manufactured in a range of sizes for different sizes of patient. Likewise, the handle portion 110 can be sized such that it is noticeably larger than the probe end 230, in order to give the illusion of smaller probe end 230 and/or colors or patterns for the probe end 230 can be selected to minimize the apparent size of the probe end 230.

In use, the bladder 235 is initially partially or completely deflated, to allow for the smallest profile for insertion. The probe end 230 inserted, while the contour 230 of the distal end of the probe end 230 gently urges the anal sphincter to expand, while the user pushes the rectal thermal monitor 200 into the rectum of the patient. The user then orients the rectal thermal monitor 200 such that the temperature sensor, which in this embodiment is on the body 231 of the probe end 230, opposite the bladder 235, is in a position with respect to the rectum wall such that the temperature of the prostate gland can be monitored. An inserter or sleeve, as will be described below in connection with FIGS. 25-29, can also be used to facilitate insertion of the rectal thermal monitor 200. The bladder 235 is then inflated by depressing the actuator 215, which is connected either to a manual pump or a valve to allow pressurized fluid to enter the bladder 235. The bladder 235, when inflated, urges the body 231 of the probe end 230 into secure contact with the rectum wall.

Upon completion of the procedure, fluid is relieved from the bladder 235. This can be achieved by depressing the actuator 215, and thereby actuating a valve to allow fluid from within the bladder 235 to be released as the rectal thermal monitor 200 is withdrawn from the rectum. Alternatively, for example, a dedicated stopcock can be provided to relieve fluid from the bladder 235. The anatomy of the rectum can help force fluid from the bladder 235, thereby collapsing the bladder 235 during removal.

Optional features of the embodiment of the rectal thermal monitor 100 of FIG. 1 can be incorporated into the rectal thermal monitor 200 of FIG. 2, and vice versa.

FIG. 3 illustrates a further embodiment of a rectal thermal monitor in accordance with the invention, which is designated generally by reference number 300. The rectal thermal monitor 300 includes a probe end 330, which includes one or more temperature sensors 331. The probe end 330 also includes a tip 335 and an angled portion 330 leading from the tip 335 to a main body 332 of the probe end 330. The probe end 330 is supported by a movable shaft 340, which in-turn is supported by a handle 310. The handle includes a contour 119 to facilitate gripping by a user, and a stop 117 to prevent excessive insertion of the rectal thermal monitor 300 into the rectum of a patient. A trigger 315 is provided to effect movement of the shaft 340 and in-turn the probe end 330. The trigger 315 can be connected to a ratchet mechanism, such that each press of the trigger 315 results in a slight distal movement of the probe end 330 with respect to the handle 310. Alternatively, other mechanisms can be provided, such as a sliding trigger, attached to the shaft 340, which engages the handle 310 to prevent undesired movement of the probe end 330.

Materials can include any of the foregoing materials set forth in connection with the embodiments of FIGS. 1 and 2. The probe end 330 is not illustrated herein as being expandable. However the probe end can include an inflatable bladder to expand the probe end 330 if desired. The probe end 330 can be somewhat compliant and resilient, and therefore, can be relatively easily inserted through the anal sphincter and into the rectum. The probe end 330 can include for example, materials such as silicone rubber and/or foam rubber to provide the desired compliance and resilience. Also, as with the foregoing embodiments, the probe end 330 can be about 2.5 inches (6.25 cm) in length and about 0.5 inches (1.25 cm) in diameter. The rectal thermal monitor 300 can be about 12 inches (30 cm) in length when the shaft 340 is fully extended.

The tip 335 can, if desired, be more rigid than the remainder of the probe end 330. Accordingly, a different material can be used for the tip 335 than for the remainder of the body portion 332. A more rigid tip 335 can enable easier initial insertion of the rectal thermal monitor 300 through the anal sphincter of the patient. Since the diameter of the tip 335 is not very large, it will not cause any substantial discomfort to the patient, but will expedite the process of insertion. The more compliant materials of the body portion 332, including of the tapered region 333 can compress during insertion, while gently urging the anal sphincter open. When fully inserted, only the shaft 340 passes through the anal sphincter. Since the shaft has a relatively small diameter, any patient discomfort is minimal.

The probe end 330 can be ratcheted by pressing trigger 315, urging the probe end 330 distally. This can help the user adjust the position of the probe end 330, and the temperature sensors 331, with respect to the rectal wall and prostate glad of the patient. In use, the probe end 330 of the rectal thermal monitor 300 can also be adjusted by depressing the trigger 315. Alternatively or additionally, the ratcheting feature can be used to snug the probe end 330 against the bottom of the rectum to orient the probe end 330 in the desired orientation. In such an embodiment, the stop 117 will contact the a buttock of the patient, serving as a guide and to secure the probe in the desired orientation within the rectum.

Upon completion of treatment, the rectal thermal monitor 300 is withdrawn. A contour 334 at a proximal end of the probe end 330 facilitates withdrawal, again, by gradually urging the anal sphincter to widen enough to allow withdrawal of the entire probe end 330.

FIGS. 4 and 5 illustrate another embodiment of a rectal thermal monitor 400 in accordance with the invention, which embodiment includes a flexible shaft 440. The probe end 430 includes a tip 435, tapered portion 433 and a body portion 432 with one or more temperature sensors, and a contoured proximal region 434 to facilitate withdrawal of the probe end 430 from the rectum, as described above in connection with the embodiment of FIG. 3. The probe end 430 can include an inflatable bladder, or can simply be made of a compliant material to provide easy insertion into and withdrawal from the rectum. A handle 410 is provided for gripping by the user. Such handle 410 can be a simple oblong shape as illustrated, or can include contours and features as shown in and described in connection with FIGS. 1-3. Further, although not explicitly illustrated, a stop, similar to stop 117 of FIGS. 1-3 can also be provided.

The flexible shaft 440 enables the user to adjust the rectal thermal monitor 400 to effectively navigate the patient's anatomy, to obtain a temperature reading of the prostate gland. The shaft 440 can be adjusted prior to commencement of insertion, or can be adjusted during insertion of the rectal thermal monitor 400. Such a capability enables the user (a physician or technician) to appropriately adjust the angle of the probe end 430 to fit the anatomy of the individual patient, thereby achieving firm contact between the rectum wall and the probe, to obtain an accurate temperature reading.

The flexible shaft 440 can include a plurality of links, secured together at junctions with a predetermined coefficient of friction therebetween, so as to provide a desired amount of rigidity to the shaft 440 as a whole. Alternatively, the shaft can include multiple bundled strands therewithin that when shaped, friction between adjacent strands helps keep the probe end 430 in the adjusted position. Alternatively still, the shaft can be made of a malleable material, such as a shape-memory polymer or temperature-sensitive polymer such as Versaflex™, but alternatively can be made of malleable metals such as aluminum or copper or corrugated non-ferrous material. If a polymer or other non-ferrous material is used, the rectal thermal monitor 400 can safely be used in an MRI field, if necessary. Alternatively still, the shaft 440 can include a material having open spaces, or slots formed therein, to allow the shaft 440 to flex along the desired axes. Such flexion, regardless of the precise implementation, can be provided about one axis, about two axes, or about an infinite number of axes.

Figure 6:
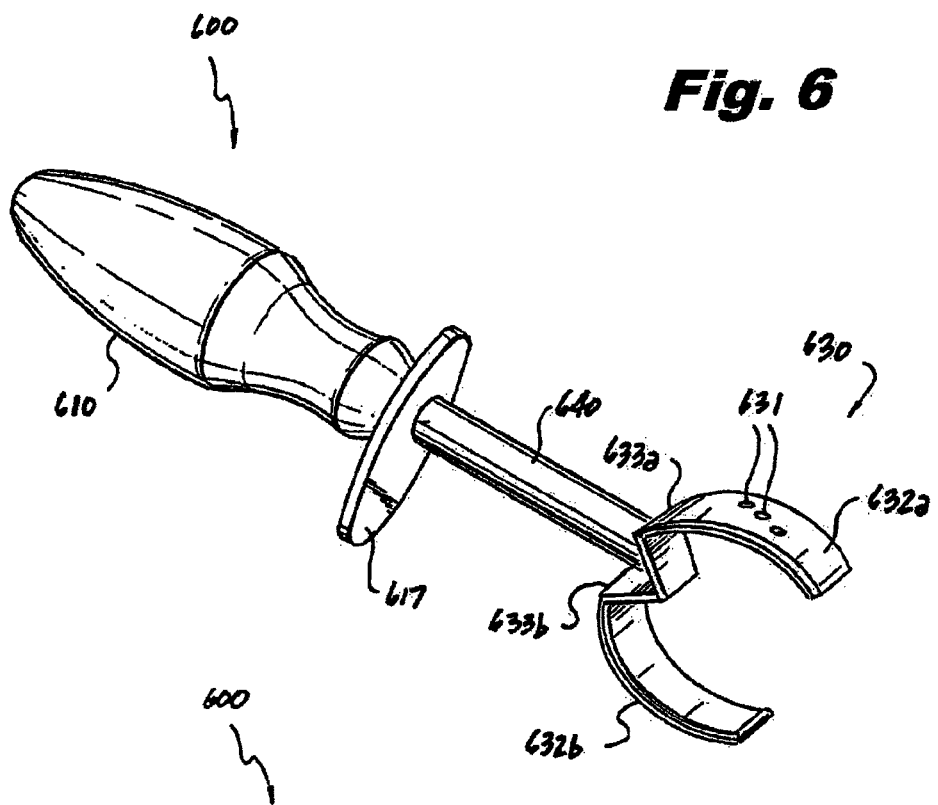
Figure 7:
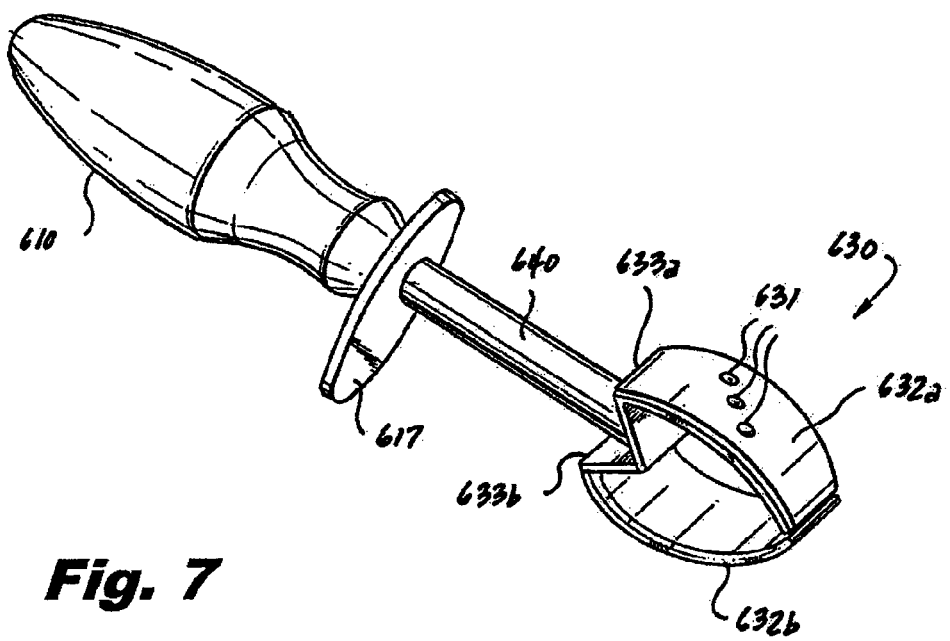

FIGS. 6-7 illustrate a further embodiment of a rectal thermal monitor (RTM) in accordance with the invention, which is indicated generally by reference number 600. The rectal thermal monitor includes a probe end 630 having flexible arms 632a, 632b at its distal end. These arms 632a, 632b each can include a hinge 633a, 633b, respectively, at its proximal end. The hinges can be so-called "living" hinges, including a compliant region and/or a line of thinned material thickness defining the hinge. Alternatively, the arms 632a, 632b can collapse simply through flexure of the arms 632a, 632b about their length.

The arms 632a, 632b can be molded in the open state illustrated in FIG. 6. Prior to insertion through the patient's anus, the arms 632a, 632b are compressed. A sleeve, as illustrated in FIGS. 25-29, inserted through the anus prior to insertion of the rectal thermal monitor 600, can facilitate insertion. The arms 632a, 632b can be curved and have a smooth surface so that the rectal thermal monitor 600 can be safely rotated about its longitudinal axis.

One or more temperature sensors 631, which can be, for example, thermocouples, are provided on one or more of the arms 632a, 632b. The arms 632a, 632b are supported by a shaft 640, which in-turn is supported by a handle 610. A stop 617 is provided to guide insertion, and to prevent the rectal thermal monitor 600 from entering the anus beyond the desired point.

The materials of the rectal thermal monitor 600 can be any of the foregoing materials, or another suitable material. While the arms 632a, 632b can be made of a resilient metallic material, the arms 632a, 632b can be made of a resilient polymeric material. The overall size of the rectal thermal monitor 600 is about 12 inches (30 cm), with the arms 632a, 632b having a diameter of about 2.5 inches (6.25 cm) in length and about 0.5 inches (1.25 cm) in diameter when expanded for sensing.

In use, a user pinches the arms 632a, 632b closed, the state of which is illustrated in FIG. 7, and inserts the rectal thermal monitor 600 through the anal sphincter of the patient. As set forth above, a sleeve, as illustrated in FIGS. 25-29, inserted through the anus prior to insertion of the rectal thermal monitor 600, can facilitate insertion. The user can then rotate the rectal thermal monitor 600 about its longitudinal axis to orient the temperature sensor(s) 630 into an appropriate orientation with respect to the prostate gland of the patient. Upon completion of the procedure, the rectal thermal monitor 600 can be withdrawn, with the proximal contour of the arms 632a, 632b, aiding the closure of the arms 632a, 632b, and easy removal.

FIG. 8 illustrates a further embodiment of a rectal thermal monitor in accordance with the invention, which is designated generally by reference number 800. The rectal thermal monitor 800 can include an inflatable bladder in its probe end 830, but can instead be static in nature, and can be made wholly or in-part of a compliant material to facilitate insertion into the patient's rectum. The probe end 830 can include a rigid or semi-rigid tip 835, and a taper 833 to facilitate insertion through the patient's anal sphincter. The body 832 of the probe end 830 can include a side taper 837, which can be provided on one or more sides of the probe end 830. A heat sink 834 with temperature sensors 831 can also be provided. The temperature sensors can be thermocouples, which are welded to the heat sink 834. The heat sink 834 and temperature sensors 831 can be insert molded into the body 832 of the rectal thermal monitor 800. As with foregoing embodiments, a proximal taper 836 can be provided to ease removal of the rectal thermal monitor from the patient's rectum.

A shaft 840 is provided, which supports the probe end 830 from the handle 810. The shaft 840 can include a contour 819 to help navigate the patient's anatomy. The handle 810 can include recessed grips 815 to enable a secure grip. The grips can include a rubberized or textured surface to facilitate a secure grip. A portion of, or the entire rectal thermal monitor 800, as with other embodiments set forth herein, can be overmolded with a layer of resilient material, such as a thermoplastic elastomer (TPE), or the like.

FIGS. 9 and 10 are enlarged views of a probe end 930, and heat sink 934, respectively, in accordance with the invention. The heat sink 934 can include apertures with temperature sensors provided therein. The temperature sensors can be thermocouples, which are welded to the heat sink 934. The heat sink 934, with the temperature sensors 931 attached can be insert molded with a body 932 of the probe end 930. The entire assembly, including the heat sink 934, temperature sensors 931 and body 932 can be overmolded with an additional material, such as a thermoplastic elastomer. As can be seen in FIGS. 9 and 10, the temperature sensors 931 can be arranged in a diagonal orientation, with respect to a heat sink 934. This arrangement allows temperature measurement at three different points. Such diagonal spacing, with respect to adjacent temperature sensors 931, increases the area of coverage for each sensor, because each sensor has a unique bidirectional coordinate.

Alternatively, the temperature sensors can be thermistors or another temperature sensor that effectively measures temperature. Non-contact type temperature sensors, such as those that measure temperature based on measurement of infra-red radiation, can be used.

FIGS. 11a, 11b, 12a, 12b, 13a and 13b illustrate an additional embodiment of a rectal thermal monitor, which is designated generally by reference number 1100. The rectal thermal monitor 1100 includes an overmolded cover 1101 over essentially the entirety of the rectal thermal monitor 1100, although variations thereof are possible. The rectal thermal monitor 1100 includes a handle 1110 at a proximal end and an expandable probe end 1130 arranged at its distal end.

As best seen in FIGS. 11a and 11b, the expandable probe end 1130 can be expanded by moving the sliding actuator 1113 distally, toward the probe end 1130. The actuator 1113 is rigidly attached to a slideable rod 1141 centrally located in the shaft 1140. The distal end of the rod 1141 includes a cam 1133, which cases the expansion of the probe end 1130, in conjunction with cam followers 1136. As the cam 1133 is moved by sliding the actuator 1113, the expanded diameter of the cam 1133 displaces the cam followers 1136 radially distally. As can be seen, the cam followers include a hinge portion 1138 that allow the followers 1136 to bend at the desired location, when expanded.

As best seen in FIGS. 11a and 11b a heat sink 1134 is provided below the surface of the overmolded cover 1101, and connected to a wire 1137, which passes through a central shaft 1105 to the handle 1110. The tip 1135 can be relatively rigid due to the proximity of the shaft 1105, relative to the end 1135, although this need not be the case. The handle 1110 can include indents 1107 or other contours to facilitate easy gripping by a user.

Figure 12A:
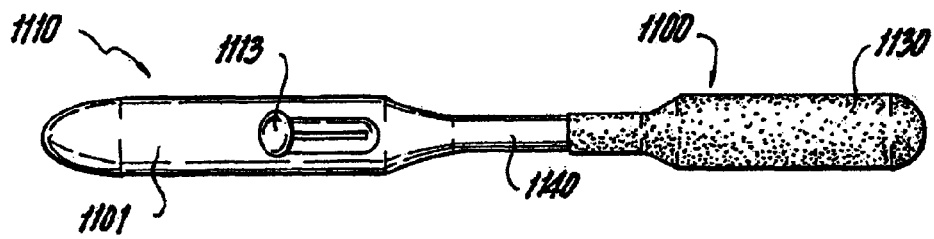
FIGS. 12a and 12b are top views of the embodiment of FIGS. 11a and 11b.
Figure 12B:
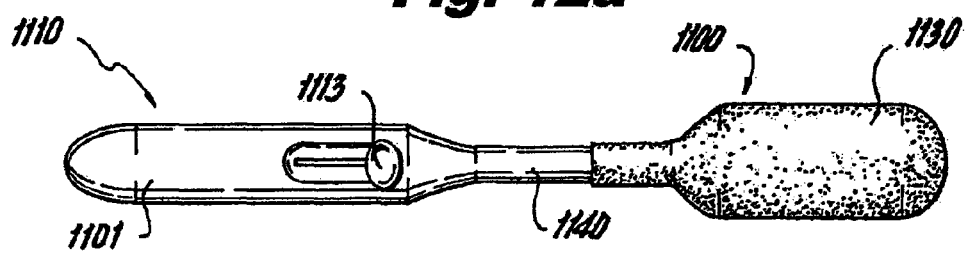
Figure 13A:
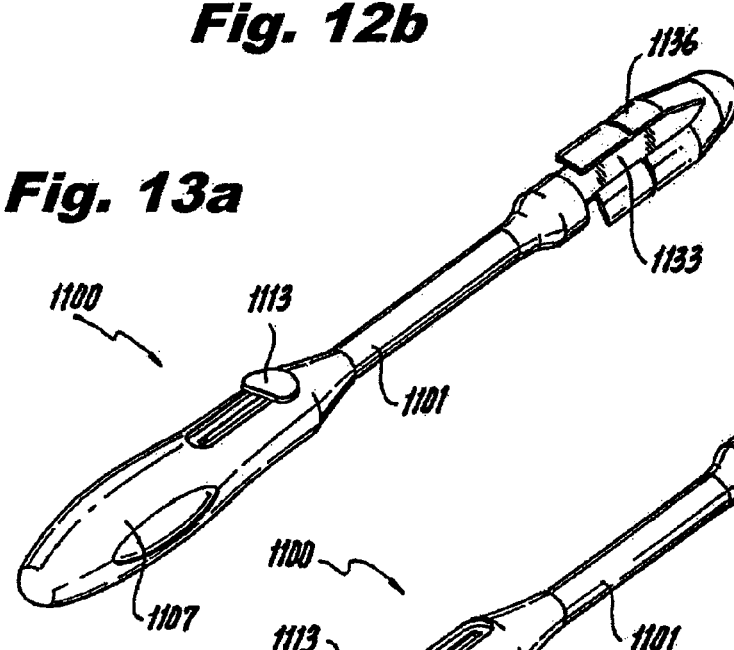
FIGS. 13a and 13b are isometric views of the embodiment of FIGS. 11a and 11b, with the outer covering removed.
Figure 13B:
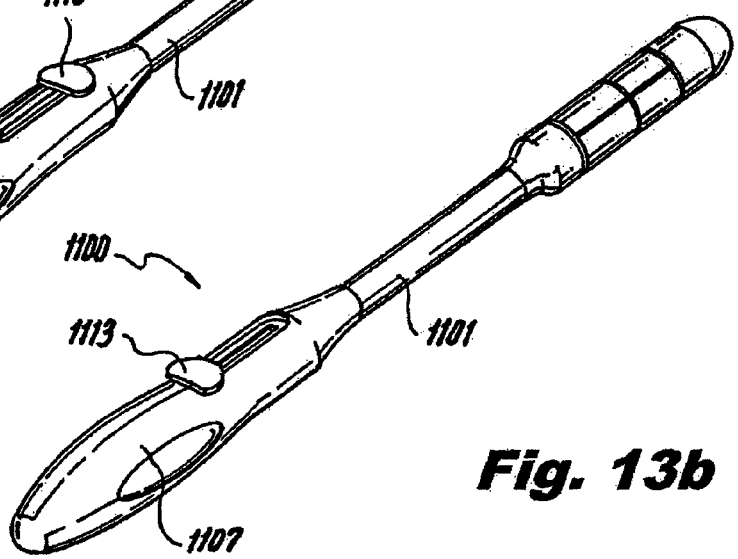
Figure 18:
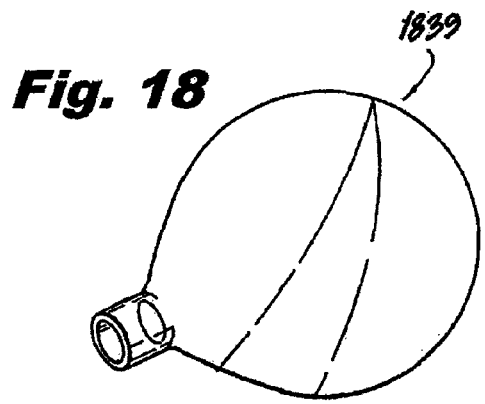
FIG. 18 is an enlarged view of the flexible sheath of the embodiment of FIGS. 14 and 15, prior to placement over the probe end of FIG. 17.
Figure 19:
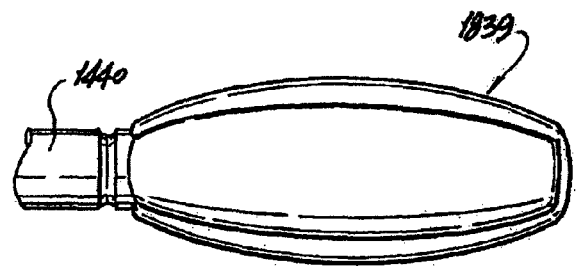
FIG. 19 is an enlarged view of the probe end of the embodiment of FIGS. 14 and 15, following placement of the sheath of FIG. 18 over the probe end of FIG. 17.

In use, the rectal thermal monitor 1100 can be inserted in its compact state, illustrated in FIGS. 11a, 12a and 13b. When inserted into the rectum, the actuator 1113 is pushed distally by the user, which expands the probe end 1130. The rectal thermal monitor 1100 can be rotated prior to or following expansion of the probe end 1130 in order to orient the heat sink 1134 into the position desired.

Materials used for the rectal thermal monitor 1100 can be any of those set forth in connection with the foregoing embodiments, but instead can be made substantially from polymeric materials. The cover 1101, or overmold portion can be a thermoplastic elastomer or other durable coating. The overall size can also be similar to the foregoing embodiments.

FIGS. 14-19 illustrate a further embodiment of a rectal thermal monitor 1400 in accordance with the invention and components thereof. FIGS. 14 and 15 are isometric views of the rectal thermal monitor 1400, illustrating a handle 1410, a shaft 1440, and a probe end 1430 held in a distal end region of the rectal thermal monitor 1400. A rigid or semi-rigid distal tip 1407 is provided, which can facilitate insertion of the rectal thermal monitor into the anal sphincter of the patient. The entire end portion of the rectal thermal monitor 1400 is covered by a resilient cover 1839. Alternatively, the tip 1407 can remained uncovered.

FIG. 16 is a detail view of the shaft 1440 in accordance with this embodiment of the invention. The shaft 1440 can be straight or curved. As seen in FIG. 17, slots 1601 are provided into which a compressible material 1731, such as a foam or foam rubber can be secured. A flexible covering 1839, as shown alone in FIG. 18, can be secured over the compressible material 1731 shown in FIG. 17, resulting in the rectal thermal monitor 1400 of FIG. 19. Prior to installation of the covering—, one or more temperature sensors are provided on or within the compressible material 1731. To prevent the covering 1839 from loosening from the shaft 1440 of the rectal thermal monitor 1400, the covering 1839 can be secured to the shaft 1440 by any suitable means, for example by heat-shrinkable material or clip.

In use, the rectal thermal monitor 1400 is inserted through the anal sphincter of the patient, with the tip 1407 facilitating opening of the anal sphincter. The compressible material 1731 allows the probe end 1430 to be relatively easily inserted through the anus and into the rectum of the patient, minimizing discomfort by compressing rather than causing the anal sphincter to expand to the full diameter of the expanded probe end 1430. However, when in the rectum, the probe end 1430 can expand to fill the rectum and thus can contact the rectum wall in the region of the prostate gland to obtain a temperature measurement thereof.

Figure 20:
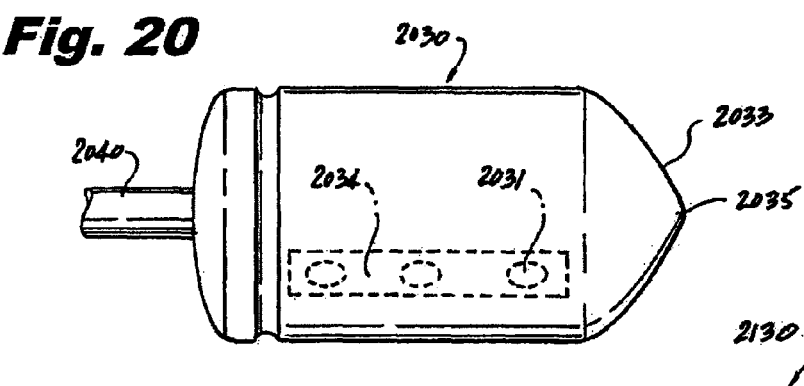
FIG. 20 is a side view of a ninth representative embodiment of a rectal thermal monitor in accordance with the present invention, which includes a coated foam end having a tapered end to facilitate insertion into a patient's rectum.

FIG. 20 illustrates a probe end 2030 in accordance with the invention. The probe end 2030 is attached to a shaft 2040, includes a taper 2033 and a tip 2035. The probe end 2030, in this embodiment is made of a foam material, covered with a resilient material such as a silicone or similar material. A heat sink 2034 with temperature sensors 2031 (shown in phantom line), is provided beneath the outer coating. As with the foregoing embodiments of similar shape, the tapered end 2033 facilitates insertion of the probe end 2030 through the patient's anal sphincter.

Figure 21:
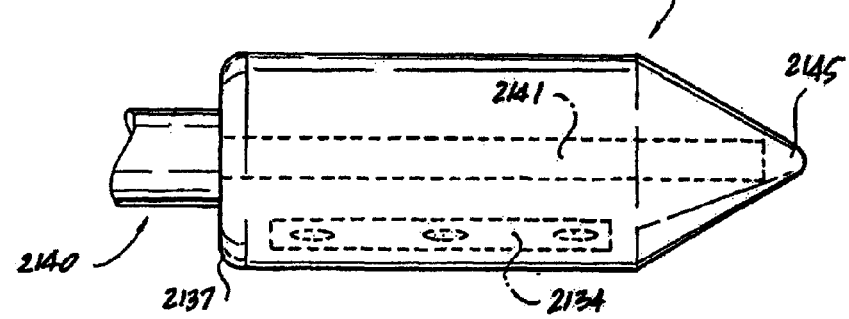
FIG. 21 is a side view of a tenth representative embodiment of a rectal thermal monitor in accordance with the present invention, which is longitudinally stretchable to reduce the cross-sectional area thereof for insertion.

FIGS. 21 and 22a-22b illustrate a rectal thermal monitor 2100 in accordance with the invention, which is capable of being stretched prior to insertion, in order to impart a lower profile to the probe end 2130. The material for the probe end 2130 can be a stretchable material such as a silicone rubber, and can be made from solidified mineral oil. A heat sink 2134 (shown in phantom line) can be provided on or beneath the surface of the probe end 2130.

An outer shaft 2140 is provided, which is secured to the proximal end 2137 of the probe end 2130. An inner shaft 2141 passes through the center of the probe end 2130, toward the distal tip 2145 of the probe end 2140. By pulling proximally (toward the user) on the outer shaft 2140, while pushing distally (away form the user) on the inner shaft 2141, the probe end 2140 is stretched, as best illustrated in FIG. 22b, resulting in a lower profile for insertion.

When stretched, the probe end 2130 can more easily be inserted into the patient's rectum. When inserted, the force is released, and the probe end 2130 expands to fill the rectum to measure the temperature of the prostate gland. For withdrawal from the rectum, the same opposite forces to stretch the probe end 2130 are applied, thus reducing the profile for removal.

FIGS. 23a and 23b illustrate a further embodiment of a rectal thermal monitor (RTM) in accordance with the invention, which is designated generally by reference number 2300. The rectal thermal monitor 2300 is expandable radially, and includes a probe end 2330 including a framework of mesh 2333. The mesh 2233 is constrained at its distal end by a tip 2335, and at its proximal end by a slideable collar 2332. The collar 2332 is rigidly secured to a sliding trigger 2313, connected thereto by any suitable interposed element, such as a rod or the like. The trigger 2313 slides along a shaft 2340 in a groove 2314. The walls of the shaft 2340 along the groove 2314 can include locking elements for engaging mating locking elements on the trigger 2313, if desired. If so equipped, the trigger can be securely latched at any location along the length of the groove 2314, thereby expanding the probe end 2330 to a desired diameter.

The tip of the rectal thermal monitor 2300 can be rigid or semi-rigid as described hereinabove. The entire probe end 2330 and the tip 2335 can be overmolded with a layer of material, or alternatively, only the mesh portion 2333 can be overmolded with such material. Alternatively still, a resilient balloon, such as one made of silicone rubber can be provided to cover the mesh 2333. One or more temperature sensors 2331 can be provided on or within the mesh 2333 of the probe end 2330. The temperature sensors 2331 can be provided in a unit attached to a backing or heat sink, or can be individually applied to the mesh 2333 to facilitate expansion and contraction of the mesh. Materials for the mesh can include, for example, a relatively rigid but resilient material, such as nylon, polypropylene, other polymer materials or non-ferrous materials.

The handle 2310 can be shaped as desired, can include a contour and/or materials to facilitate gripping by the user, or any other feature set forth herein in connection with other embodiments of the invention. A sensor cable 2311 is permanently or removably secured to the proximal end of the rectal thermal monitor 2300, to interface with the treatment equipment. Such a feature can be provided with any of the embodiments set forth herein.

In use, the rectal thermal monitor 2300 is inserted through the anal sphincter of the patient, with the help of tip 2335, which aids in dilating the anal sphincter. Once inserted into the rectum, the trigger 2314 is moved distally, toward the probe end 2330, which causes the collar 2332 to move distally, which in-turn causes the mesh 2333 to expand radially outwardly. The rectal thermal monitor 2300 is then oriented within the rectum such that the temperature sensors 2331 are in thermal communication with the region of the rectum wall closest the prostate gland, to obtain an accurate temperature reading. Withdrawal of the rectal thermal monitor 2300 is the reverse of insertion, with the trigger 2313 first being moved proximally to collapse the probe end 2330, and the rectal thermal monitor 2300 then being removed from the rectum.

Figure 24A:
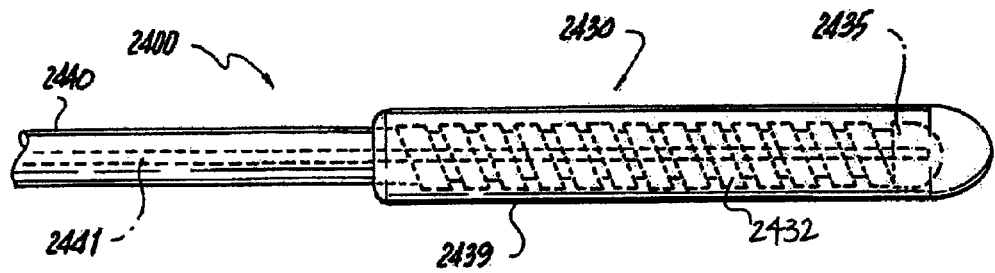
FIGS. 24a and 24b are side views of a twelfth representative embodiment of a rectal thermal monitor in accordance with the present invention, which includes an expandable probe end made of a spiral component, such that when twisted with either expand or contract.
Figure 24B:
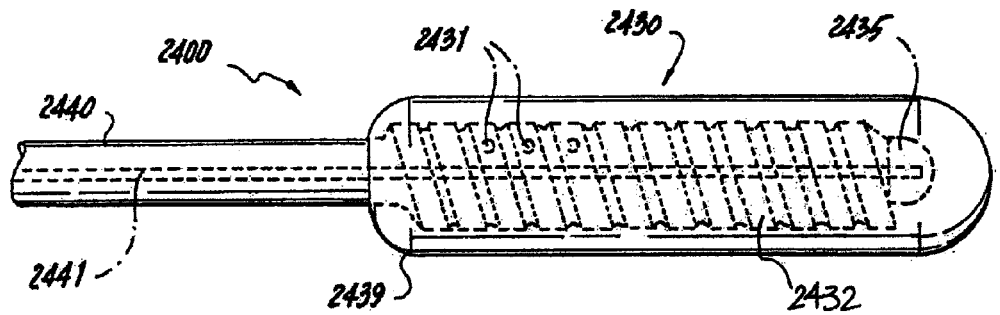

FIGS. 24a and 24b illustrate a further embodiment of a rectal thermal monitor in accordance with the invention, which is designated generally by reference number 2400. The rectal thermal monitor 2400 includes a spiral expandable probe end 2430, which is arranged between the distal tip 2435 and an outer shaft 2440. An inner shaft 2441, shown in phantom line is rigidly fixed to the tip 2435, such that when the inner shaft 2441 and outer shaft 2441 are oppositely rotated, expansion or contraction of the spiral probe end 2430 is achieved.

The spiral spring 2432 of the probe end 2430 can be made of any suitable resilient material. Resilient metals, metal alloys or shape-memory alloys can be used, but a resilient polymeric material can be used. The probe end 2430 can be formed to be in its expanded state, shown in FIG. 24b, when the spring 2432 is relaxed, that is, not under compression or tension.

Temperature sensors 2431 are provided in predetermined locations on the spring 2432 of the probe end 2430, such that when the probe end 2430 is in its expanded state, the temperature sensors 2431 are in the desired location, relative to one another.

As with other embodiments set forth herein, a resilient cover 2439, made from a material such as silicone rubber is provided on top of the probe end 2430, and can further cover the shaft 2440 and a handle portion if desired.

In use, the rectal thermal monitor 2400 is tensioned such that it is in the compact state illustrated in FIG. 24a. The rectal thermal monitor 2400 is then inserted into the rectum of the patient. The inner or outer shaft is then rotated, or simply released, such that the spring 2432 relaxes and the probe end 2430 expands. Upon completion of treatment, the shafts 2440, 2441 are rotated relative to one another to compress the spring, to facilitate withdrawal.

The shafts 2440, 2441 can be coaxial and can be actuated by the user in any suitable manner. The inner shaft 2441 can be rigidly attached to a handle, as set forth above, while the coaxial outer shaft can rotate around the inner shaft, terminating at its proximal end, opposite the tip 2435, at a collar or other easily gripped element, which can be rotated by the user. Such collar can be latched relative to the handle (not shown) and thus relative to the inner shaft 2441.

FIGS. 25-29 illustrate insertion sleeves that can be used to facilitate insertion of rectal thermal monitors (RTM) in accordance with the invention. The sleeves are particularly useful when inserting a passively collapsible rectal thermal monitor.

Figure 25:
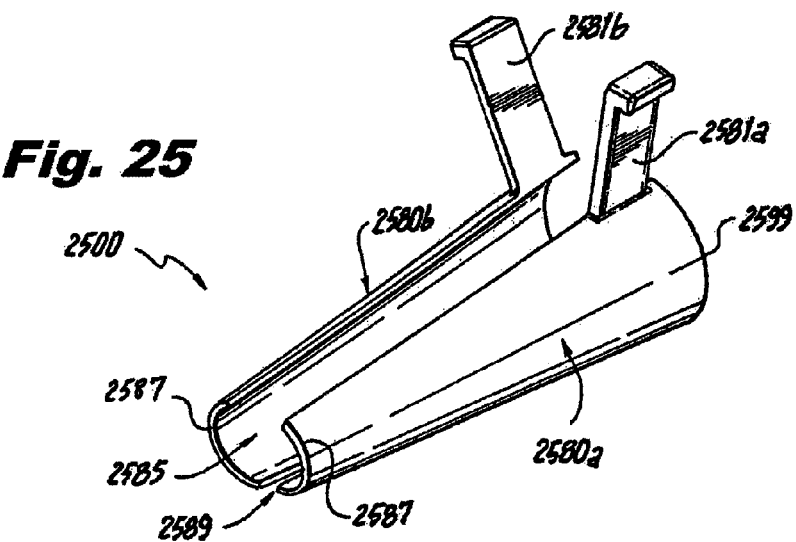
FIG. 25 illustrates an inserter device in accordance with the invention, which can facilitate insertion of rectal thermal monitors in accordance with the invention through the anal sphincter and into the rectum of a patient. The inserter of this embodiment is provided with two separable halves.

FIG. 25 illustrates an inserter or sleeve 2500 in accordance with the invention, which is made from a rigid or semi-rigid material or materials. An insertion lumen 2585 is defined between two sleeve halves 2580a, 2580b. A hinge can be provided along the lower junction 2589 to connect the two sleeve halves and so that the sleeve 2500 can be removed from the rectal thermal monitor once the rectal thermal monitor is inserted. Handles 2581a, 2581b are defined at a proximal end of the sleeve 2500, and allow the user to securely grip the sleeve 2500 during a procedure. The sleeve 2500 is provided with a contour 2587 on its outer surface 2588, which tapers toward its distal end 2587. The inner lumen 2585 also narrows approaching the distal end of the sleeve 2500, which is inserted through the anal sphincter of the patient.

In use, the sleeve 2500 is inserted through the anal sphincter of the patient, with the user grasping the handles 2581a, 2581b. A probe is inserted through the proximal end 2599 of the lumen 2585. As the probe traverses the length of the sleeve 2500, the probe end is compressed, such that it fits into through the distal end 2587 of the lumen 2585 and into the rectum of the patient. Once the probe end is inserted, the sleeve 2500 can be withdrawn along the shaft of the rectal thermal monitor, and when fully outside of the patient, the halves 2580a, 2580b can be separated, or hinged apart, and removed from the shaft of the rectal thermal monitor.

FIGS. 26a and 26b illustrate a sleeve 2670 and a rectal thermal monitor 2631 having a compressible probe end 2630. In FIG. 26b, the probe end 2630 is compressed within a sleeve 2670, and in FIG. 26a, the probe end 2630 is pushed out of the sleeve 2670, and expanded. Such a sleeve 2670 can be used in conjunction with any of the foregoing embodiments, and is particularly advantageous in use with passively compressible rectal thermal monitors. In use, the probe 2601 is inserted into the sleeve 2670, or alternatively is provided already in the sleeve. The sleeve 2670 and probe 2630 are then inserted together through the anal sphincter and into the rectum of the patient. A tip 2635 of the probe 2601 can facilitate the initial entry through the anal sphincter. The distal end of the sleeve 2691 can be provided initially open, or initially sealed closed, as illustrated in FIGS. 27 and 29. The probe 2601 can be oriented with respect to the sleeve 2670, such that the tip 2635 just protrudes past the distal end 2691 of the sleeve 2670, so that that tip 2635 can facilitate insertion.

FIGS. 27 and 28 illustrate a further embodiment of an insertion sleeve in accordance with the invention, which is designated generally by reference number 2700. A probe end 2730 and shaft 2740 is shown traversing the sleeve 2700. A flared proximal end 2706 is provided to facilitate insertion of the probe end 2730 into the sleeve 2700. The sleeve further includes a rupturable end 2708, which can be pushed through by the probe end 2730, when reached. A lubricious coating can be provided on the inner surface of the sleeve to facilitate movement of the probe end 2730. A longitudinal line of weakness, perforation or other feature can be provided to facilitate removal of the sleeve 2700 from the probe, once the probe is inserted into the rectum. Alternatively, the sleeve 2700 can be left in place until completion of the procedure.

In use, the sleeve 2700 is inserted through the anal sphincter of the patient, which can be accomplished by way of a small-diameter inserter or similar device. Once inserted, the probe end 2730 is inserted into the sleeve 2700. The probe end traverses the length of the sleeve 2700. Insertion is eased in comparison with embodiments without the use of such a sleeve 2700, since longitudinal forces against the anal sphincter are essentially eliminated, leaving only radially outward forces to urge the anal sphincter open, which greatly reduces patient discomfort. When the probe end 2730 reaches the end 2708 of the sleeve 2700, the user need only push a little further to rupture the end of the sleeve 2700, and gain access to the rectum.

Materials used for the sleeve 2700 can be materials that are radially expandable, but not excessively expandable in the longitudinal direction. This enables passage of the probe end 2730, while preventing undesired elongation of the sleeve 2700 during insertion, thereby ensuring effective insertion of the rectal thermal monitor. Accordingly, materials can include any suitably compliant material, such as silicone rubber or composite material for example.

FIG. 29 illustrates a sleeve 2900, substantially similar to the sleeve 2700 of FIGS. 27 and 28. However, the sleeve 2900 includes longitudinally strengthening ridges 2904, arranges around the circumference of the sleeve 2900, parallel to the length thereof. The ridges 2904 prevent excessive longitudinal elongation of the sleeve, by providing increased resistance to longitudinal stretch. However, flat sections 2901 are provided about the axis to enable substantial radial expansion of the sleeve 2900 when a probe end passes therethrough. Similarly to the embodiment of sleeve 2700 of FIGS. 27 and 28, a flared proximal end 2901 and rupturable distal end 2908 are provided. In use, the sleeve 2900 functions substantially similarly to the sleeve 2700 of FIGS. 27 and 28. Materials can include any suitably compliant material, and can be composite materials, with the ribs being at least partially made of a less compliant material than the remainder of the sleeve 2900.

At least some of the disclosed embodiments according to the invention relate to rectal thermal monitors and accessories therefore that can effectively sense the temperature of the rectum wall, while still enabling relatively easy and less painful insertion, minimizing discomfort to the patient. Various features of the disclosed embodiments can be changed, deleted, and/or mixed in various combinations even if not expressly disclosed herein. This disclosure is exemplary and not limiting.

The invention claimed is:

1. A rectal thermal monitor for transrectal prostate temperature measurement, the probe comprising:
    a handle arranged in a proximal end portion of the monitor for gripping by a user;
    an elongate shaft extending from the handle;
    an expandable distal probe portion arranged on a distal end of the shaft, at a position opposite the handle portion, shaped to facilitate insertion through an anal sphincter and into a rectum of a patient, the expandable distal probe portion including two probe halves and an inflatable bladder, each of the two probe halves arranged on a separate half of the shaft and configured to be slideable with respect to the other, each of the two probe halves disposed on an external portion of the shaft, the inflatable bladder arranged between the probe halves and configured to separate the probe halves;
    a cover element, covering at least a portion of the distal probe portion, the cover element being made from a resilient material; and
    a temperature sensing element arranged within the distal probe portion, beneath the cover element, adapted and configured to sense a temperature of the prostate of the patient through the rectum wall of the patient.

2. The monitor of claim 1, wherein each of the two probe halves includes a tapered distal end to facilitate insertion through the anal sphincter.

3. The monitor of claim 1, wherein the temperature sensing element is attached to a heat sink to facilitate temperature measurement of an increased area.

* * * * *